(12) United States Patent
Kappeler et al.

(10) Patent No.: US 9,897,619 B2
(45) Date of Patent: Feb. 20, 2018

(54) ANALYTE EXTRACTION APPARATUS AND METHOD

(71) Applicants: Sphere Medical Limited, Cambridge, Cambridgeshire (GB); UCL Business PLC, London, Greater London (GB)

(72) Inventors: Natascha Kappeler, London (GB); Rachel Anne McKendry, London (GB); Russell Keay, Cambridgeshire (GB); David Pettigrew, Cambridgshire (GB); Steven Andrew Fowler, Cambridge (GB); Daren Joseph Caruana, London (GB)

(73) Assignees: Sphere Medical Limited (GB); UCL Business Plc (GB)

( * ) Notice: Subject to any disclaimer, the term of this patent is extended or adjusted under 35 U.S.C. 154(b) by 101 days.

(21) Appl. No.: 14/768,421

(22) PCT Filed: Feb. 17, 2014

(86) PCT No.: PCT/GB2014/050451
§ 371 (c)(1),
(2) Date: Aug. 17, 2015

(87) PCT Pub. No.: WO2014/125300
PCT Pub. Date: Aug. 21, 2014

(65) Prior Publication Data
US 2016/0003858 A1    Jan. 7, 2016

(30) Foreign Application Priority Data
Feb. 18, 2013 (GB) .................................. 1302774.3

(51) Int. Cl.
| | |
|---|---|
| *C12Q 1/26* | (2006.01) |
| *G01N 33/50* | (2006.01) |
| *G01N 33/94* | (2006.01) |
| *G01N 21/78* | (2006.01) |
| *G01N 21/77* | (2006.01) |

(52) U.S. Cl.
CPC ......... *G01N 33/9446* (2013.01); *G01N 21/78* (2013.01); *G01N 2021/7783* (2013.01)

(58) Field of Classification Search
CPC .... G01N 33/50; G01N 33/9446; G01N 33/94; G01N 21/77; G01N 21/75; G01N 2021/783; G01N 2021/7769
USPC ..................... 422/67, 63, 50; 436/53, 52, 43
See application file for complete search history.

(56) References Cited

U.S. PATENT DOCUMENTS

| | | | | |
|---|---|---|---|---|
| 6,153,400 A | * | 11/2000 | Matsumura | .......... G01N 21/253 435/283.1 |
| 6,251,624 B1 | * | 6/2001 | Matsumura | .............. C12Q 1/04 435/29 |
| 2001/0055786 A1 | * | 12/2001 | Arnold | ..................... C12Q 1/26 435/25 |

FOREIGN PATENT DOCUMENTS

| | | |
|---|---|---|
| WO | 00/23806 A1 | 4/2000 |
| WO | 2012/049486 A1 | 4/2012 |

OTHER PUBLICATIONS

International Search Report for corresponding application No. PCT/GB2014/050451, dated Apr. 2014.
Beckman Coulter Inc. "Emit 2000 Vancomycin Assay" Sep. 1, 2000, pp. 1-3; XP055109950.
Department of Health & Human Services USA: "Roche Online TDM Vancomycin", May 11, 2006, pp. 1-6, XP05510995.
K. Balakrishnamurali: "Studies on Development and Validation of Analytical Procedures for the Estimation of Selected Drugs Through New RP-HPLC Methods. Ph.D. thesis" Jan. 1, 2010, XP055109702.

* cited by examiner

*Primary Examiner* — Christine T Mui
(74) *Attorney, Agent, or Firm* — Wood, Phillips, Katz, Clark & Mortimer

(57) ABSTRACT

Disclosed is a method and apparatus for determining a concentration of a glycopeptide antibiotic containing a phenol moiety such as Vancomycin in a complex sample matrix by extracting the glycopeptide antibiotic from a metered portion of the complex sample matrix by exposing said metered portion to an extraction material having an affinity with the glycopeptide antibiotic; and exposing the extraction material to a metered portion of an eluent for releasing the glycopeptide antibiotic from the extraction material; and by determining a concentration of the glycopeptide antibiotic by adding a Gibbs reagent (2,6 dichloroquinone-4chloroimide) to the metered portion of the complex sample matrix or the eluent; activating the Gibbs reagent and, after the reaction between the activated Gibbs reagent and the antibiotic has stabilized; detecting the reaction product of the activated Gibbs reagent and the antibiotic in said eluent; and determining the concentration of the antibiotic in the complex sample matrix from the detected reaction product. A method of designing a personalized drug administration regime using the thus obtained concentration is also disclosed.

16 Claims, 11 Drawing Sheets

(A) Formula: $C_{72}H_{76}Cl_4N_{10}O_{25}$

```
mass    %
1620   59.8
1621   49.9
1622  100.0
1623   71.8
1624   68.9
1625   41.4
1626   25.1
1627   12.2
1628    5.2
1629    1.9
1630    0.6
1631    0.2
1632    0.0
```

(B)

ANALYTE EXTRACTION APPARATUS AND METHOD

FIELD OF THE INVENTION

The present invention relates to a method and apparatus for improving the automation of cell lysis for use in the extraction and measurement of analyte concentrations in biological samples. In particular, this invention provides a means for automatically diluting and lysing blood cells prior to Vancomycin extraction and analysis.

BACKGROUND OF THE INVENTION

Since their discovery, antibiotics have become critical in the fight against infectious diseases caused by bacteria. However their extensive and inappropriate use is one of the biggest drivers of drug resistance; see. e.g., Davies, S., Infections and the Rise of Antimicrobial Resistance, Annual Report of the Chief Medical Officer—Volume Two, 2011; Chan, M., Combating Antimicrobial Resistance: Time for Action conference, WHO, 2013; and J. W. Ndieyira et al. in Nature Nanotechnology 3(11), pages 691-696, 2008.

The emergence of new infections and the re-emergence of old enemies, such as antibiotic-resistant hospital 'super-bugs', methicillin-resistant *Staphylococcus aureus* (MRSA) and Vancomycin-resistant Enterococci (VRE), and the associated increase in fatalities, is a major global healthcare problem, costing the NHS alone £1bn per annum. At the same time, the antibiotic-pipeline has nearly dried up with just a few new classes of antibiotics discovered over the last forty years; see e.g. M. A Cooper et al., Nature 472, page 32, 2011 and M. S. Butler et al. in Journal of Antibiotics 64(6), pages 413-425, 2011. This lack of new potent drugs puts us at risk of returning to the pre-antibiotic era of untreatable infections, or as the WHO recently forecasted "the world is heading for a post-antibiotic era". Therefore, there is an urgent need for tools to improve the stewardship of antibiotics to minimise the evolutionary pressure on bacteria, which inevitable leads to antimicrobial drug resistance.

In clinics, the administrated drug concentrations for many drugs, including (glycopeptide) antibiotics, relies on a combination of clinical judgment, averaged pharmacokinetic models and subjective methods of assessing the effect of the therapy, resulting in an inherent variability in the quality of therapy. The administration of many therapeutic drugs, for example a glycopeptide antibiotic such as Vancomycin, is routinely guided by therapeutic drug monitoring (TDM) which can be significantly improved with more frequent monitoring, particularly in the first 24 hours of administration. Conclusively, there is an urgent need for new technologies to tailor treatments to individual patients' needs, particularly patient populations at risk, such as paediatrics, obese, elderly, immune-compromised, intensive care unit (ICU) and oncology patients.

Furthermore, in the special case of the glycopeptide antibiotic Vancomycin with its possible nephrotoxicity, patients which receiving concomitant nephrotoxic drugs are at high risks of undesirable toxic side effects. Therefore especially for those patients, there is an urgent need for monitoring drug levels at the point-of-care within minutes in order to personalise and optimise therapy at the patient level.

This need has been recognized as early as 2002; see C. M. Tobin et al., Journal of Antimicrobial Chemotherapy, 50(5), pages 713-718, 2002. The British National Formulary (BNF) recommends peak serum values for Vancomycin to be in the range of 25 to 40 µg/ml which corresponds to 17.3 to 27.6 µM of Vancomycin, and trough values should be in the range of 10 to 15 µg/ml and 15 to 20 for complicated infections which corresponds to 6.9 to 10.4 µM and 10.4 to 13.8 µM Vancomycin respectively. For paediatrics the peak serum values can reach 60 µg/ml, which corresponds to 41.4 µM of Vancomycin, and trough values are typically measured in the range of 5 to 10 µg/ml which corresponds to 3.5 to 6.9 µM Vancomycin.

The state-of-the-art in clinics for therapeutic Vancomycin monitoring requires extensive sample preparation and often the samples have to be sent to a specialised laboratory with trained staff. This is expensive, laborious, time-consuming, and leads to inevitable delays between tests and results, which means important therapeutic decisions are delayed and patient pathways can be slow and cumbersome, as also recognized by M. A Cooper et al., Nature 472, page 32, 2011 and by C. M. Tobin et al., Journal of Antimicrobial Chemotherapy, 50(5), pages 713-718, 2002.

Furthermore, routine drug monitoring only measures the total antibiotic concentration even though protein binding varies dramatically (10-82% protein bound) with 55% often quoted as the mean fraction bound; see e.g. Zeitlinger et al., Antimicrobial Agents and Chemotherapy 55(7), pages 3067-3074, 2011. Since measurement of the free Vancomycin concentration requires several preparation steps and is consequently very time consuming and expensive, it is not routinely performed in health care facilities see e.g. Berthoin et al., International Journal of Antimicrobial Agents 34(6), pages 555-560, 2009. This is problematic as it is generally accepted that only the free drug fraction is pharmacologically active and the fraction of drug bound to serum proteins is inactive. Moreover, studies have suggested that the correlation between free and total fraction is poor, see e.g. Estes & Derendorf, European Journal of Medical Research, 15(12), pages 533-543, 2010 and Butterfield et al. Antimicrobial agents and Chemotherapy 55(9), pages 4277-4282 2011.

The current gold standards in therapeutic Vancomycin drug monitoring are:
  fluorescence polarisation immunoassay (FPIA), such as the "FLx/TDx" from Abbott Diagnostics, UK.
  homogenous enzyme immunoassay, such as the "ONLINE TDM Vancomycin assay" from COBAS®, Roche, CH.

In 2002, NHS Bristol launched a survey to study Vancomycin therapeutic drug monitoring (TDM) as disclosed by C. M. Tobin et al., Journal of Antimicrobial Chemotherapy, 50(5), pages 713-718, 2002. They questioned 310 participants from UK NHS hospitals, UK public health laboratories, UK private hospitals and other European and non-European hospitals. According to this survey, the cost of a Vancomycin assay including taking blood, transport to the laboratory (since microbiology departments are still the main providers of assays), time for paperwork, running the assay, result reporting and interpretation was estimated to cost around £35, which exceeds the drug costs for twice-daily 1 g intravenous dosing.

Moreover the Tobin study showed that around 65% of all assays only received their results in one day. Almost exclusively, 97% of the respondent were using the fluorescence polarisation immunoassay (FPIA) purchased from Abbott Diagnostics, Maidenhead, UK.

Furthermore a recent study published by Touw et al. in European Journal of Hospital Pharmacy Science, page 13, 2007, presented the results of cost-effectiveness study of therapeutic drug monitoring (TDM). Their study published results on aminoglycoside and Vancomycin treatments and showed a statistically significant higher death rate (6.3%), longer stays in hospitals (12.3%), higher hearing loss (46.3%) and renal impairment (34.0%), and consequently higher total charges (6.3%) in hospitals that did not have pharmacist-managed therapies, which includes TDM combined with results interpretation by using mathematical and pharmacokinetic models and then advising the physicians correspondingly. Conclusively they recommend that Vancomycin therapy is guided by TDM, especially in patient populations at risk such as ICU patients, oncology patients and patient receiving concomitant nephrotoxic medicines.

It is therefore clear that there is a long-felt need for more facile and accurate detection of antibiotic levels, and in particular glycopeptide antibiotic levels in the complex sample matrix of a patient at the point of care, and in particular Vancomycin levels, to facilitate rapid TDM at the point-of-care. In particular, a need exists to accurately detect free (unbound) and bound fractions of glycopeptide antibiotics in such complex sample matrices at the patient's point of care.

SUMMARY OF THE INVENTION

The present invention seeks to provide a method and apparatus for automating the detection of glycopeptide antibiotics comprising a (poly)phenolic functional group, e.g. Vancomycin, that can produce reliable detection of levels of such glycopeptide antibiotics in a complex sample matrix of a patient, e.g. blood, plasma or serum, at the point-of-care.

In accordance with an aspect of the present invention, there is provided a method of determining a concentration of an antibiotic containing a phenol moiety, i.e. at least one phenol moiety, in a complex sample matrix. The method comprises extracting the glycopeptide antibiotic from a metered portion of the complex sample matrix by exposing said metered portion to an extraction material having an affinity with the glycopeptide antibiotic; and exposing the extraction material to a metered portion of a first eluent being a first organic solvent or a second eluent being a second organic solvent/water mixture for releasing the glycopeptide antibiotic from the extraction material; and determining a concentration of the glycopeptide antibiotic by adding an excess amount of Gibbs reagent (2,6 dichloroquinone-4-chloroimide) relative to the amount of the glycopeptide antibiotic to the metered portion of the first or second eluent; activating the Gibbs reagent under alkaline conditions and, after the reaction between the activated Gibbs reagent and the antibiotic has stabilized; detecting the reaction product of the activated Gibbs reagent and the antibiotic in said first or second eluent; and determining the concentration of the antibiotic in the complex sample matrix from the detected reaction product, said concentration being the concentration of unbound antibiotic in the complex sample matrix in case of the first eluent; and the concentration of bound antibiotic in the complex sample matrix in case of the second eluent.

It has surprisingly been found that a glycopeptide antibiotic containing phenol moieties such as Vancomycin can be effectively extracted from a complex sample matrix using an extraction assay that has been previously used for the extraction of Propofol from such a sample matrix; see WO 2012/049486 A1.

Moreover, it has surprisingly been found that an appropriate choice of eluent can selectively extract the free or bound glycopeptide antibiotic fraction using such an extraction assay, as it has been found that the affinity of the glycopeptide antibiotic with the extraction material in the assay depends on whether the glycopeptide antibiotic is bound to the extraction material only as is the case for the free fraction, or whether the glycopeptide antibiotic is bound to the extraction material and/or to matter extracted from the complex sample matrix such as cellular material, extracellular material, e.g. proteins, fatty acids, glucose, urea, lactic acid, electrolytes and so on, as is the case for the bound fraction. Therefore, the free and bound fraction of glycopeptide antibiotics such as Vancomycin can be accurately determined with a single assay.

In addition, it has surprisingly been found that the Gibbs reaction can be used for a phenolic glycopeptide antibiotic such as Vancomycin in order to obtain a reaction product that can be electrochemically or colorimetrically detected. This is unexpected since the para-unsubstituted position (position 6) of the dihydroxy benzene (which is the $7^{th}$ residue of the glycopeptide antibiotics) in such antibiotics, and in the particular case of Vancomycin, is sterically hindered, which prima facie suggests a low chance of successfully completing the Gibbs reaction for such antibiotics. This method enables a much better control of drug delivery at the point-of-care and leads to the improved management of infections, patient treatment, safety and health outcomes, as well as curbs the incorrect usage of antibiotics that fuels resistance. It provides frequent, fast and accurate information throughout patient treatment as well as reduces the therapeutic decision time.

At this point, it is noted that the abstract of Rao et al. in Indian pharmacist 2(9), page 59-61, 2003 and the thesis titled "Studies on Development and Validation of Analytical Procedures for the Estimation of Selected Drugs through new Rp-HPLC methods" by K. Bala Murali Krishna, Acharya Nagarjuna University, chapter 3 on page 69, 2010 [http://shodhganga.inflibnet.ac.in/handle/10603/8209] suggest the formation of the Vancomycin-Gibbs reaction product by performing the Gibbs reaction in an acidic medium. They obtained a yellow coloured product with maximal absorbance wavelength ($\lambda_{max}$) at 400 nm and 460 nm respectively in the aforementioned citations. However, the present inventors have found that such a yellow coloured product corresponds to the activated Gibbs reagent rather than the Gibbs-Vancomycin reaction product.

In contrast, the present inventors have realized that the desired Gibbs-Vancomycin reaction product may be formed under alkaline reaction conditions, which produces a distinct purple/magenta product that has a maximal absorbance wavelength ($\lambda_{max}$) in the range of 580-600 nm.

Embodiments of the present invention enable detection of glycopeptide antibiotics containing phenol moieties such as Vancomycin at clinically relevant concentrations (3.5-27.5 μM or 5-40 μg/ml) with lower detection limits comparable to the aforementioned gold standard Roche Cobas Vanc2 assay (1.2 μM), with the clear benefit that drug quantification is achieved within minutes, compared to several hours when having to send samples for analysis with laboratory-based assays.

The first and/or the second organic solvent may be methanol.

In an embodiment, said exposing step is performed with the first eluent, the method further comprising repeating the exposing and determination steps with the second eluent. In this manner, both the free and bound fractions of the glycopeptide antibiotic in the complex sample matrix can be determined from the first and second eluents respectively.

In a particularly advantageous embodiment, the method further comprises exposing the extraction material to at least one washing step prior to exposing the extraction material to said metered portion of the first and/or second eluent to remove weakly bound impurities from the extraction material in order to remove weakly bound impurities from the extraction material that can interfere with the Gibbs reaction.

The complex sample matrix may comprise matter such as cellular and extracellular material as previously explained, in which case the exposing step may comprise providing a known quantity of the complex sample matrix; diluting said known quantity with a lysing agent, said lysing agent having an osmotic pressure lower than the osmotic pressure of the cellular material; and subsequently feeding the diluted known quantity through a filtering stage comprising the extraction material after a predetermined amount of time to separate the glycopeptide antibiotic from the destabilized matter, e.g. cellular and extracellular material, by adhering the glycopeptide antibiotic to the extraction material.

The extraction material may further comprise a sorbent material for mechanically lysing the cellular material, said sorbent material having an affinity for binding the glycopeptide antibiotic such as a reverse phase sorbent material, such as C8, C12, C18 or Strata-X.

In an embodiment, the detecting step comprises electrochemically detecting the reaction product of the activated Gibbs reagent and the glycopeptide antibiotic.

In an alternative embodiment, the detecting step comprises colorimetrically detecting the reaction product of the activated Gibbs reagent and the glycopeptide antibiotic. This is particularly advantageous as the reaction product can be readily detected without the need for any further reaction. For instance, for Vancomycin, said colorimetrically detecting comprises measuring the intensity of the absorption at 589 nm.

The Gibbs reaction may be performed at any suitable point in time, e.g. following said extracting step.

The complex sample matrix is not necessarily retrieved from a (human) patient. In an alternative embodiment, the complex sample matrix is obtained from a food product such as milk or meat, which facilitates the rapid determination of glycopeptide antibiotic levels in such food products, which improves the ease with which food standards may be controlled, as the presence of (excessive amounts of) glycopeptide antibiotics in such food products is prohibited in most jurisdictions.

In accordance with another aspect of the present invention, there is provided a method of providing a personalized administration regime of a glycopeptide antibiotic containing a phenol moiety for a patient, the method comprising determining the concentration of the glycopeptide antibiotic in a complex sample matrix of said patient in accordance with an embodiment of the glycopeptide antibiotic concentration determining method of the present invention; deriving metabolic characteristics of the glycopeptide antibiotic for said patient from the determined concentration of the glycopeptide antibiotic in said complex sample matrix; and providing said personalized glycopeptide antibiotic administration regime based on said metabolic characteristics.

This enables the drug dose to be administered, e.g. titrated, to the desired target concentration according to patient's individual drug adsorption, distribution, metabolism and excretion, detect accumulation or changes in the drug clearance rate and provide early detection of faults in the drug delivery system. Consequently monitoring drug levels at the point-of-care will be a key tool in individualising, optimising and managing therapy at the patient level, and therefore provide an important step from passive "monitoring" towards (pro-)active management of drug concentrations in patients.

In an embodiment, the determining step comprises periodically determining the concentration of the glycopeptide antibiotic in a complex sample matrix, wherein said deriving step comprises deriving said metabolic characteristics from a trend in the periodically determined concentrations.

In accordance with yet another embodiment of the present invention, there is provided an apparatus for automatically extracting of a glycopeptide antibiotic containing a phenol moiety from a complex sample matrix comprising matter such as cellular and extracellular material, the apparatus comprising a sample reception stage having on output for providing a defined quantity of the complex sample matrix; a mixing stage having a first input in fluidic connection with the output of the sample reception stage, a second input for receiving a lysing agent and an output for providing a mixture of the defined quantity of the complex sample matrix and the lysing agent;

a delay stage having an input in fluidic connection with the output of the mixing stage and an output for providing the delayed mixture of the defined quantity of the complex sample matrix and the lysing agent; a filtering stage comprising a sorbent material for mechanically lysing the cellular material, said sorbent material having an affinity for binding of the glycopeptide antibiotic, said filtering stage having an input in fluidic connection with the output of the delay stage; and a controller for controlling the flow rate of the mixture of the defined quantity of the complex sample matrix and the lysing agent through said delay stage, wherein the apparatus further comprises a colorimetric measurement stage in fluid connection with the filtering stage and arranged to determine the colorimetric spectrum of an eluent received from the filtering stage including a reaction product of the glycopeptide antibiotic and the activated Gibbs reagent; and a processor coupled to the colorimetric measurement stage adapted to derive a concentration of the glycopeptide antibiotic in the complex sample matrix from a specific wavelength in the colorimetric spectrum.

Such an apparatus can automatically detect the level of a glycopeptide antibiotic with one or more phenolic moieties such as Vancomycin in such a complex sample matrix, thus facilitating an improved control of drug delivery at the point-of-care and improved management of infections, patient treatment, safety and health outcomes, as well as the curbing of the incorrect usage of antibiotics that fuels resistance by providing frequent, fast and accurate information throughout patient treatment and reduce the therapeutic decision time. The apparatus provides combined osmotic and mechanical lysis inside the apparatus and, preferentially achieving the mechanical lysis by passing the diluted sample across a sorbent with affinity for the analyte of interest. This approach enhances the efficiency of the release of a glycopeptide antibiotic containing phenol moieties such as Vancomycin onto the sorbent. In addition, the apparatus is constructed such that any sample material being accumulated on top of the sorbent is still available for the subsequent glycopeptide antibiotic extraction and detection/measurement.

In addition, the novel apparatus provides for more efficient use as it allows the injection of a whole complex sample matrix into the instrument without the requirement for pre-treatment or dilution. This has the important advantage that the actual volume of lysing agent used does not need determining, as the metering is performed on the actual complex sample matrix, such that the amount of glycopeptide antibiotic extracted from the sample diluted by the lysing agent directly corresponds to the amount of glycopeptide antibiotic present in the complex sample matrix; i.e. the amount of lysing agent used is irrelevant other than for the purpose of ensuring that the cellular material is sufficiently destabilized, e.g. ruptured.

In an embodiment, the specific wavelength is in the range of 580-600 nm, and preferably is 589 nm in case of the glycopeptide antibiotic containing phenol moieties being Vancomycin.

The sample reception stage may comprise a metering device such as a rotary valve for extracting a known quantity of a complex sample matrix received at the input of the sample reception stage. This reduces the required amount of reagents such as the lysis agent as the sample evaluation is performed on a portion of the sample only.

The apparatus may further comprise a fluid reservoir in fluid connection with the filtering stage for providing the filtering stage with a washing agent for removing materials that would interfere with the subsequent extraction of the glycopeptide antibiotic from the sorbent material. This further improves the accuracy of the glycopeptide antibiotic, e.g. Vancomycin, detection with the apparatus.

The filter stage may be comprised in a solid phase extraction cartridge to facilitate reusability of the apparatus of the present invention at minimal cost overhead as such reusable cartridges can be manufactured at a small cost.

In an embodiment, the sorbent material is a reverse phase sorbent material, such as C8, C12, C18 or Strata-X as such materials have an affinity for binding glycopeptide antibiotics containing one or more phenolic moieties. Strata-X is particularly suitable for binding Vancomycin.

BRIEF DESCRIPTION OF THE EMBODIMENTS

Embodiments of the invention are described in more detail and by way of non-limiting examples with reference to the accompanying drawings, wherein:

FIG. 1 schematically depicts a flowchart of an embodiment of the measurement method of the present invention incorporating the novel sample preparation approach;

FIG. 2 schematically depicts an embodiment of the device of the present invention incorporating the novel sample preparation method;

DETAILED DESCRIPTION OF THE DRAWINGS

Figure 1:
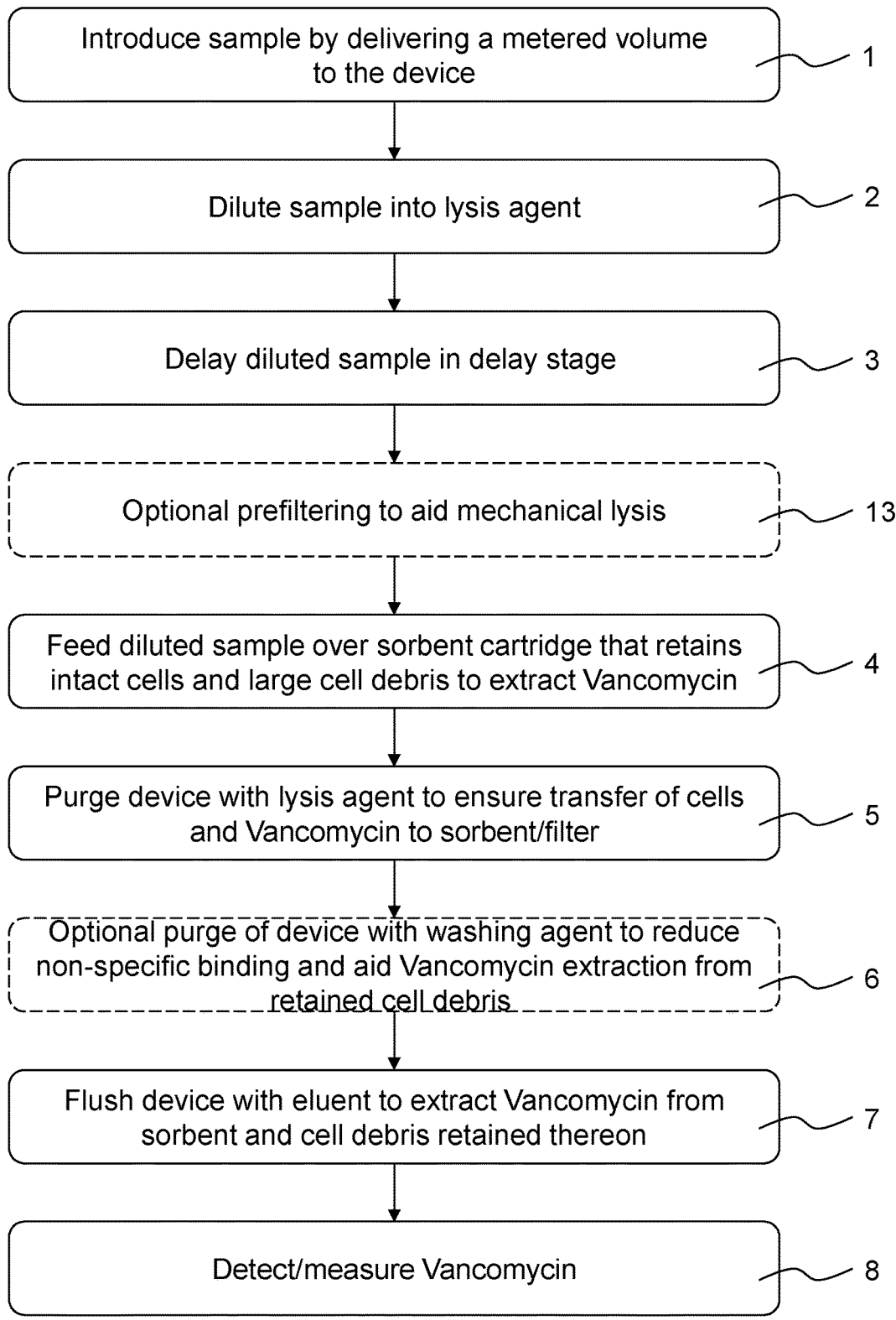

It should be understood that the Figures are merely schematic and are not drawn to scale. It should also be understood that the same reference numerals are used throughout the Figures to indicate the same or similar parts.

The invention can be applied to situations where a glycopeptide antibiotic analyte of interest such as Vancomycin has to be extracted from a complex, in particular a biological, sample. It is in particular applicable to the extraction of glycopeptide antibiotic species from blood or food samples. In these samples, some of the analyte or analytes of interest contained in the sample will typically be bound to constituents of the sample, for example, blood cells or proteins. In order to measure the concentration of the analyte or analytes in the sample, the analyte or analytes will often have to be extracted from these constituents during a sample preparation step prior to the actual detection or measurement step. While the invention will be illustrated primarily with respect to extraction of a glycopeptide antibiotic such as Vancomycin from blood samples, it is equally applicable to other complex sample matrices, e.g. samples containing matter such as cells or similar structures.

In general, embodiments of the present invention employ a combination of dilution, osmotic lysis and mechanical lysis to break up cells and make the analyte of interest bound to the cell components available for analysis. In order to achieve this aim, the sample is initially diluted using a lysing agent, for example de-ionised water, solutions containing detergents, urea, acids or combinations thereof; the actual choice of lysing agent will depend on the characteristics of the sample and suitable agents are known to those trained in the art of cell lysis. The dilution step will result in the cells contained in the blood sample taking on components of the lysing agent (e.g. water) and therefore swelling or breaking up. The cells contained in the sample will therefore either burst and release their content, or will be in a more fragile state (e.g. in the form of erythrocyte ghosts in the example of osmotic lysis by the dilution into water).

Following a delay stage (typically of the order of seconds to several minutes), the diluted sample will then be passed through a solid phase extraction cartridge. An additional pre-filter may also be incorporated just before the SPE cartridge. The advantage of such a pre-filter over the prior art is that it may also be used for mechanical lysis and exposed to subsequent extraction of the analyte of interest using a suitable eluent as it is placed in the fluid lines of the apparatus of the present invention.

The shear forces introduced by the action of the SPE cartridge or the filter/SPE cartridge combination serves to increase the lysis efficiency by breaking up the intact erythrocytes, erythrocyte ghosts and other cell fragments that remained after the dilution into the lysis agent. The composition of the sorbent in the cartridge or pre-filter is chosen such that it is able to bind the analyte of interest, i.e. a glycopeptide antibiotic such as Vancomycin, in preference to the components of the sample matrix. The combined action of diluting the sample with a lysing agent and lysing the remaining cells by shear force increases the availability of the analyte of interest for extraction onto the sorbent of the solid phase extraction column.

There is also the possibility of some components of the sample matrix (e.g. unlysed cells or fragments thereof) being accumulated on top of the sorbent bed or pre-filter and not being passed through the sorbent. In a subsequent step, the sorbent cartridge is washed using one or more suitable washing agent(s). The choice of washing agent will depend on the analyte of interest; the washing agent should preferentially remove interferents from the sorbent and sample material accumulated on top of the sorbent bed, while leaving the analyte of interest bound to the sorbent or filter material.

Additionally, in one embodiment of the invention, the washing agent will assist in the break up of the accumulated cell debris on the sorbent bed and increase the availability of the analyte for extraction.

Following the washing step, the analyte of interest is eluted from the sorbent, pre-filter and/or the materials accumulated on top of the sorbent/filter material. This elution step employs a suitable extraction agent that is able to dissolve the analyte of interest from the sorbent or filter material as well as from the material left behind on top of the sorbent or filter. As will be demonstrated in more detail later, it may be possible to selectively extract a particular fraction of the analyte of interest from the sorbent using appropriate eluents; for instance, an analyte of interest bound only to sorbent material may be removed using a different eluent compared to an analyte of interest bound to sorbent material and/or cellular material present in the complex sample matrix.

The eluent is then passed into a detection chamber where the analyte of interest is detected or the amount of the analyte of interest in the eluent is quantified. A range of detection or measurement techniques are available depending on the analyte of interest. For example, in the case of Vancomycin as an example of a glycopeptide antibiotic, colorimetric or electrochemical detection techniques may be used.

The glycopeptide antibiotic of interest is detected as a reaction product of its reaction the activated Gibbs reagent. The proposed reaction scheme 1 is depicted below for glycopeptide antibiotics containing phenol moieties such as Vancomycin. It is noted that this is a proposed reaction scheme only that has not been verified such that an alternative reaction scheme may apply.

Reaction Scheme 1

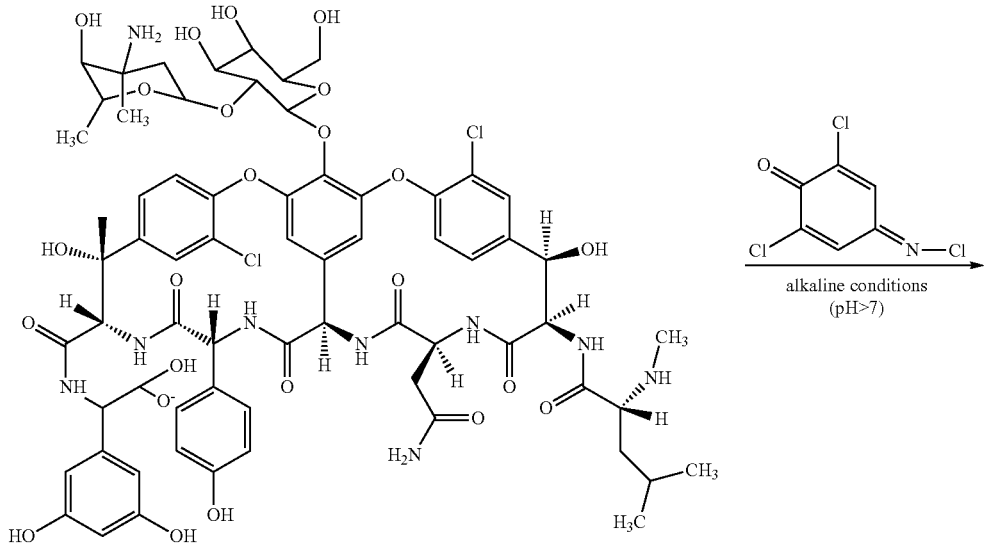

-continued

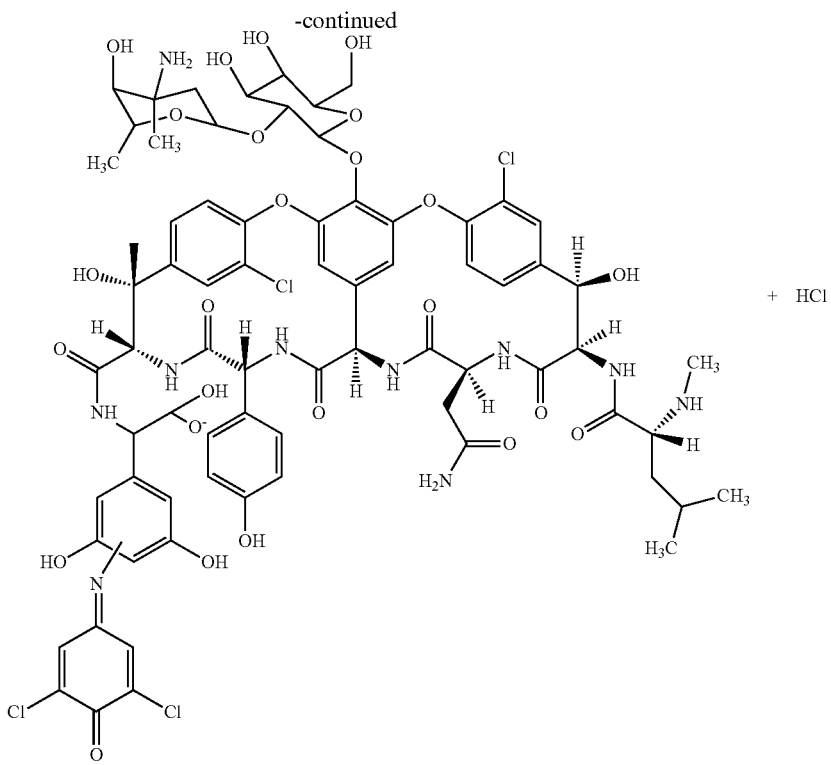

+ HCl

This however does not influence the teachings of the present invention as it has been demonstrated (see examples) that the Gibbs reaction can be effectively performed between Vancomycin and the activated Gibbs reagent when performing the Gibbs reaction under alkaline conditions (i.e. pH>7) using an excess of the Gibbs reagent wherein the excess preferably is limited to five times the molar amount of the Gibbs reagent relative to the molar amount of the glycopeptide antibiotic to avoid the formation of such different products and fragments.

Figure 2:
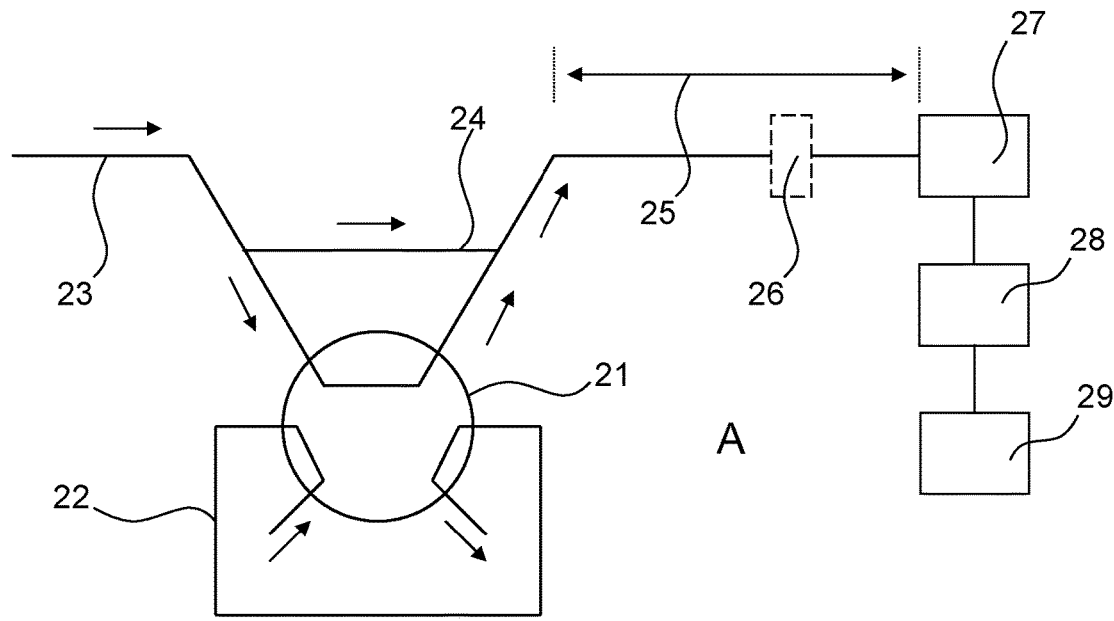
Figure 2:
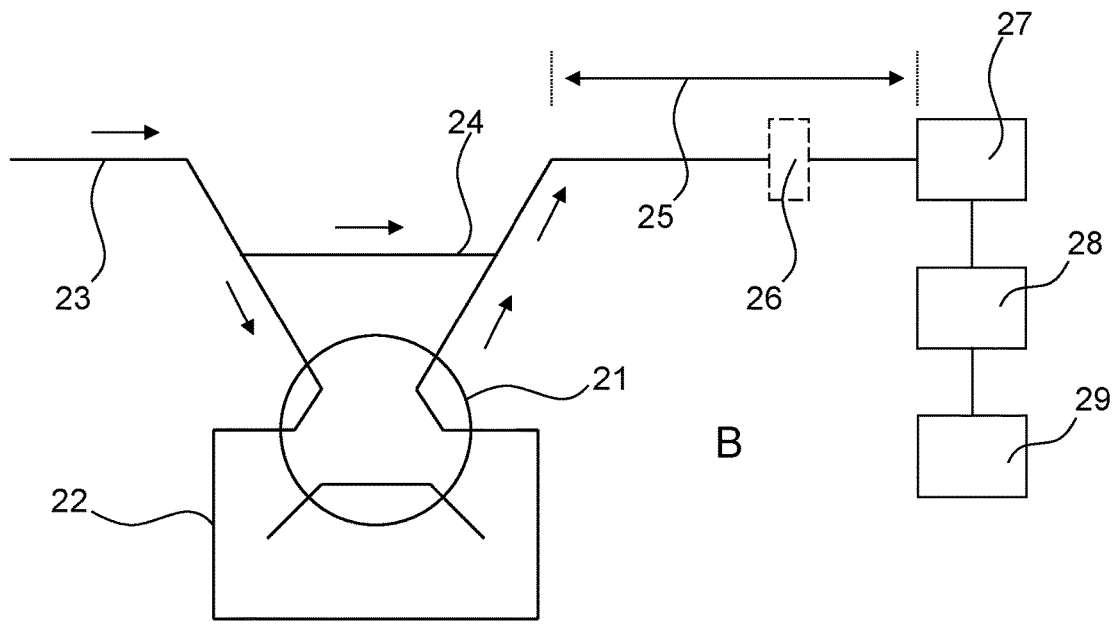

One non-limiting embodiment of the present invention is described in more detail in FIG. 1 in conjunction with FIG. 2, which shows an apparatus 20 capable of implementing this method. This embodiment comprises the following steps, some of which are optional as indicated by the dashed boxes in FIG. 1. It should be noted that where reference is made in the following to water as an eluent or washing agent, this is intended to refer to water per se as well as to aqueous buffers.

1. Introducing a Sample Volume to the Fluidic System

The sample introduced into the apparatus 20 in any suitable manner, e.g. either in a manual or automated fashion.

If concentration measurements are being made by the apparatus 20, it is preferred that a known volume of this sample is made available for further processing by the apparatus 20. Metering a known volume from the sample may be achieved using a sample metering module 21. An example suitable implementation of a method of delivering a known volume includes, but is not limited to, a 6 port, 2 position rotary valve connected to the fluidic system. This valve can be used to switch a length of tubing 22 containing a known volume of the sample of interest into the rest of the fluidic system. This is shown in FIG. 2 as valve position A. Other methods of introducing a known sample volume to a fluidic system will be known to those who are skilled in the art.

Alternatively, a known volume of sample may be introduced either manually or automatically in the first place.

In one particular embodiment, the sample is a sample of body fluids, for example, blood, plasma, serum, urine, saliva, cerebral fluids and so on. In another embodiment, the sample may be a food product or food product extract, e.g. milk or a meat extract.

In a preferred embodiment of the invention, the sample contains the drug Vancomycin as the analyte of interest, as the inaccurate determination of this drug in such samples can seriously impair the effectiveness of the drug administration regime, and can cause micro-organisms becoming resistant to such antibiotics as explained in more detail above. The method and the device of the present invention enable the extraction of glycopeptide antibiotics with phenol functional groups, e.g. Vancomycin, from such samples with unparalleled accuracy, which facilitates the detection of such glycopeptide antibiotics e.g. through colorimetry by performing the Gibbs reaction on the glycopeptide antibiotics as will be explained in more detail later.

2. Dilution of the Sample into an Lysing Agent

The blood sample or parts thereof, for example, the metered volume of the sample, are subsequently mixed with a lysing agent, which may be introduced into the apparatus 20 via tubing 23. The lysing agent is chosen dependent on the sample and the subsequent extraction step. It can, for example, be de-ionised water, aqueous salt solutions with an osmolarity lower than that of the sample, solutions containing ammonium chloride, detergents, urea, acids or combinations thereof. In situations where the analyte of interest (Vancomycin) is subsequently to be extracted by reverse phase, osmotic lysis by dilution into de-ionised water is preferred.

The dilution itself may be achieved through the use of a known length of tubing that bypasses the sample metering module, such as the tubing 24 shown in FIG. 2. The relative resistances of the sample metering and bypass lines are chosen to allow for dilution of the sample, for example a dilution between a 1-fold and 100-fold dilution of the sample (preferably 15-fold). The exact dilution of a given sample will vary depending on its viscosity. Methods of tuning the relative resistances will be known to those who are skilled in the art, and may include, but are not limited to, controlling the length and internal diameter of the tubing and the incorporation of a flow restrictor. Such principles are known per se e.g. from the field of microfluidics and will not be explained in further detail for the sake of brevity only.

3. Providing Time for the Sample and the Lysis Agent to Mix and React with each Other In order to enable the lysis agent and the sample to interact with each other, the diluted sample is given some time before it is passed to the mechanical lysis stage 27 in FIG. 2. This time period depends on the sample being investigated and the nature of the lysis method being employed, but is preferentially of the order of one second to several minutes. This period should be sufficiently long for any cells contained in the diluted sample to be fragile enough for the mechanical lysis stage.

This delay period may be generated by a delay stage, such as delay stage 25 as shown in FIG. 2. This delay stage 25 preferably consists of a defined length of tubing, which, in conjunction with a controlled rate of fluid flow, allows the sample to incubate for a period of time.

4. Mechanical Lysis of the Diluted Sample

After the delay stage 25, the diluted sample is passed across a mechanical lysis stage 27. The purpose of this mechanical lysis stage 27 is to mechanically lyse (break up) the remainder of the cells, the erythrocyte ghosts and the cell membrane fragments by shear forces. The primary purpose of this step is to facilitate the release of the antibiotic of interest, e.g. Vancomycin, from the cells, cell components and cell membranes, thereby making it more available for subsequent extraction onto the sorbent. The secondary purpose of this stage is to ensure that large intact cells and cell fragments that remain after the initial chemical/osmotic and mechanical lysis steps are retained until they can be broken up sufficiently for efficient analyte extraction from them during subsequent steps (e.g. steps 6-8).

In one preferred embodiment, the mechanical lysis stage 27 consists of a solid-phase extraction cartridge containing a suitable sorbent. The sorbent may be in powdered or in co-sintered form. It may be held in place using a suitable frit. Preferably, the solid phase extraction sorbent should also be capable of extracting the analyte of interest from the lysate. In another embodiment, a filter 26 or a combination of a filter 26 and a solid phase extraction sorbent may be used, with the filter 26 providing a pre-filtering step 13 to aid the mechanical lysis by also retaining intact cells and large cell fragments. Porous materials, including, but not limited to, glass/metallic/polymer fibres, powders or sintered polymer membranes may be used as filters for the mechanical lysis. Other methods of producing porous materials will be known to those who are skilled in the art. Passing the diluted sample through the sorbent and/or porous material will apply shear forces to the cells and cell fragments which will break up the cells. Other methods of applying shear force will be known to those who are skilled in the art.

The diluted and lysed sample is then brought into contact with a suitable sorbent or filter material. The composition of the sorbent or filter material is chosen such that it is able to bind the glycopeptide antibiotic of interest, e.g. Vancomycin, in preference to the diluted and lysed sample. The purpose of this step is to extract the analyte of interest from the sample and bind it to the sorbent or filter material.

In one embodiment of the invention, the sorbent or filter 26 and the mechanical lysis stage 27 are combined in one unit. In a preferred embodiment of the invention, the sorbent or filter is used as the porous material in the mechanical lysis stage.

For example, in the case of Vancomycin being the analyte of interest, a reverse-phase sorbent cartridge is preferred, made from materials known to those trained in solid phase extraction and including materials, such as C18, C8 and Strata-X.

In a preferred embodiment of the invention, the sorbent is contained in a solid-phase extraction cartridge.

5. Purging of the Sample Metering and Bypass Sections

After all the diluted sample has been transferred to the mechanical lysis/analyte extraction module via the delay stage, the sample metering, bypass, delay and mechanical lysis sections can then be flushed with a large excess of the lysing agent to ensure that all sedimented cells are purged from these lines and transferred to the extraction stage. To this end, the valve 21 is placed in position B as shown in FIG. 2.

6. Washing Step

The sorbent cartridge and/or filter may then be washed using one or more suitable washing agent(s). The purpose of this washing step is to remove any substance which may interfere with the subsequent detection of the analyte of interest from the material adsorbed in the sorbent cartridge or filter. A first washing step with water may be applied to remove weakly bound impurities. This washing step may be repeated if necessary, e.g. two washing steps with 1 ml de-ionized water may be applied for this purpose. The washing step is found to significantly improve the accuracy of the determination of the free and bound fraction of the glycopeptide antibiotic (Vancomycin) by suppressing unwanted Gibbs reactions, e.g. with weakly bound impurities, in particular proteins.

This may be followed by a second washing step with pure organic solvents, e.g. methanol, to remove lipophilic and hydrophobic species that may interfere with the Gibbs coupling reaction and may lead to cross-contamination, such as, but not limited to, propofol.

The second washing step may be collected in case the concentration of the free (unbound) glycopeptide antibiotic such as Vancomycin is to be determined using an organic solvent such as methanol as eluent as previously explained. In this case, although it may be difficult to completely rule out unwanted (competing) Gibbs reactions in this scenario (see example 5 below), the use of excess amount of Gibbs reagent ensures that the concentration of the unbound glycopeptide antibiotic can be accurately determined by ensuring that a sufficient amount of Gibbs reagent remains to react with the glycopeptide antibiotic.

The first and second washing steps may be repeated if necessary, e.g. by performing a number of first washing steps prior to performing a number of second washing steps. Only the first of the second washing steps may require collecting to determine the concentration of the free (unbound) glycopeptide antibiotic such as Vancomycin although the eluents of multiple second washing steps may be combined for the same purpose.

7. Extraction of the Analyte of Interest from the Sorbent or Filter

Standard techniques are then used to extract the analyte of interest from the sorbent or filter and the sample materials left behind on top of the sorbent and/or filter. For example, a known volume of a suitable solvent which preferentially dissolves/binds the analyte of interest with respect to the sorbent and/or filter may be passed through the sorbent and/or filter to remove the analyte of interest from the sorbent and/or filter. These techniques will be known to those who are skilled in the art.

In the case of Vancomycin being the analyte of interest, methanol may be used to extract unbound Vancomycin from a sorbent such as a reverse phase sorbent material, e.g. Strata-X, whereas a volume of 1 part (by volume) water and two parts (by volume) methanol may be used to extract Vancomycin bound to serum constituents of the complex sample matrix from a sorbent such as a reverse phase sorbent material, e.g. Strata-X; other suitable extraction agents and methods of extraction are known to those trained in the art of solid phase extraction.

In the special case of separate quantification of free and bound, e.g. protein-bound Vancomycin concentrations, a volume of organic solvent such as methanol may be used as a first eluent and collected for the free concentration quantification. This may then be followed by the use and collection of a volume of 1 part (by volume) water and two parts (by volume) methanol, which removes the bound fraction of the Vancomycin of the sorbent and/or filter.

8. Detection or Concentration Measurement of the Analyte of Interest in the Eluent The eluent from the sorbent and/or filter is passed into a detection stage 28 where the concentration of the analyte in the extract, and hence the original concentration in the blood sample, can then be determined using a suitable detection system. The detection system required will vary depending on the analyte of interest. In a particularly preferred embodiment, the detection stage 28 comprises a colorimeter for determining the colorimetric spectrum of the Gibbs reaction product with the phenol moiety-containing antibiotic of interest. The colorimetric detection of the Gibbs reaction product involving propofol is disclosed by McGaughran et al in Journal of Clinical Monitoring and Computing, vol. 20, no. 5, pp. 381-381, 2006, which teachings apply mutatis mutandis. Other suitable methods for analyte detection may include, but are not limited to, electrochemical, fluorescent or gravimetric approaches. Other methods of detection will be known to those who are skilled in the art. It has been found (see below) that the reaction between the glycopeptide antibiotic and the Gibbs reagent is particularly successful if an excess Gibbs reagent is used. About a 5-fold excess is particularly preferred as previously explained.

The generated spectrum may be collected by a processor 29, which determines the glycopeptide antibiotic concentration in the complex sample matrix from the intensity of the absorption in the range of 580-600 nm and preferably at 589 nm for Vancomycin or another appropriate wavelength in case of the Gibbs reaction product of the activated Gibbs reagent with another phenol functional group containing glycopeptide antibiotic. The processor 29 may form part of the detection stage 28 or may be separate to the detection stage 28. Consequently, a fully automated method and apparatus for determining the concentration of a phenol moiety-containing glycopeptide antibiotic such as Vancomycin in a complex matrix within minutes at low cost is provided.

It is noted that it will be clear that the apparatus of the present invention may comprise other useful features, such as one or more reservoirs in fluid communication with the detection stage 28 for containing the respective reagents for performing the Gibbs reaction on the eluent. Respective metering devices may be present between the reservoirs and the detection stage 28 for metering the amounts of reagents fed into the detection stage 28. Such metering devices may for instance be controlled by the processor 29 or another processor.

The proof of concept of the successful extraction of free (unbound) and bound Vancomycin from a whole serum sample using the method of the present invention will be demonstrated with the aid of the following examples. It should be understood that these examples are not intended to limit the scope of the invention and that variations to this example, e.g. the use of another sample type or another glycopeptide antibiotic are feasible without departing from the teachings of the present invention.

Synthesis Example 1

Figure 3:
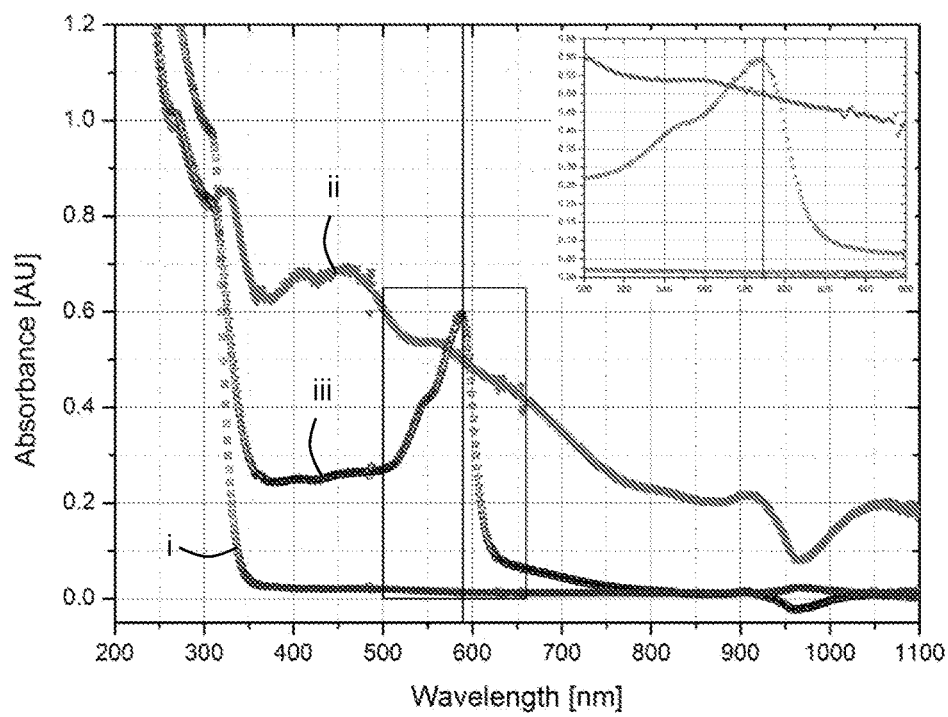
FIG. 3 depicts absorption characteristics of the reaction of Vancomycin with an equimolar amount of Gibbs reagent.

In order to demonstrate that the present inventors have developed a protocol under which glycopeptide antibiotics such as Vancomycin can react with the activated Gibbs reagent, 0.8 mM of Vancomycin was dissolved in a borate buffer (0.4 M NaOH) and reacted with an equimolar amount of the activated Gibbs reagent in a mixture of methanol and borate buffer under alkaline conditions. FIG. 3 shows the UV-vis spectra of the two starting products, Vancomycin (i) and the activated Gibbs reagent (ii), and the novel purple/magenta coupling product (iii). The maximal absorbance wavelength ($\lambda_{max}$) of the newly formed coupling product is 589 nm (highlighted by the box in FIG. 3) and its concentration can be calculated via the Beer-Lambert law. The reaction was repeated with increasing amounts of Gibbs reagent (Vancomycin:activated Gibbs reagent molar ratios 1:2, 1:3, 1:4, 1:5 and 1:65) to demonstrate that a completed coupling reaction is achieved when using excess Gibbs reagent.

Figure 4:
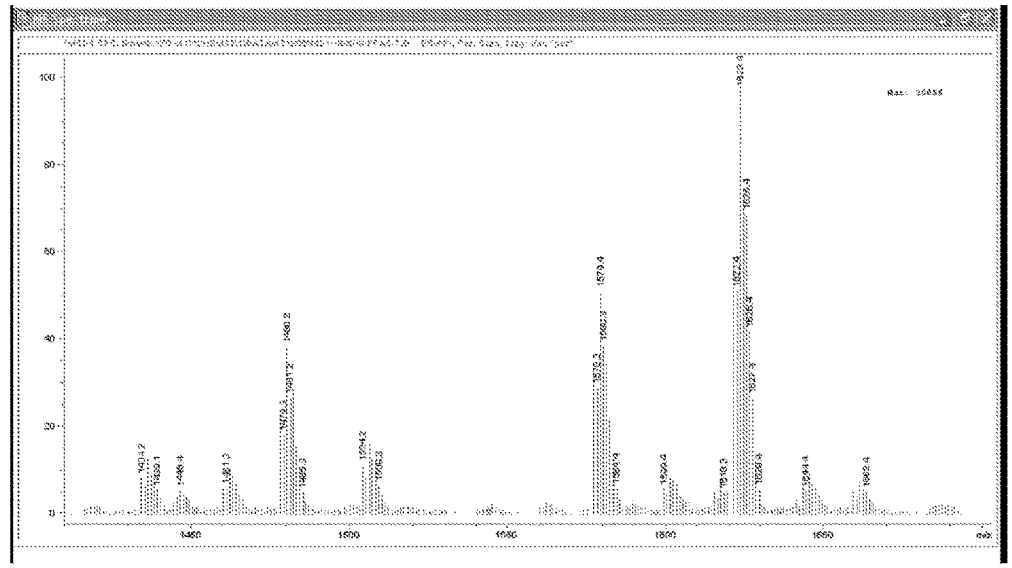
FIG. 4 (A) shows the theoretical prediction of the isotopic pattern of mass from the novel coupling product ($C_{72}H_{76}Cl_4N_{10}O_{25}$) based on 1:1 stoichiometric ratio of Vancomycin:Gibbs under alkaline condition, whereas (B) shows the experimentally measured mass spectrum of the novel reaction product.

The top panel of FIG. 4 shows the theoretical prediction of the isotopic pattern of mass from the novel coupling product ($C_{72}H_{76}Cl_4N_{10}O_{25}$) based on 1:1 stoichiometric ratio of Vancomycin:Gibbs under alkaline conditions. The bottom pane of FIG. 4 shows the experimentally measured mass spectrum of the novel reaction product. The mass spectrum was determined using an Agilent 1100 series G1946D with an electrospray ionisation (ESI) probe from Agilent (Agilent, Santa Clara, Calif., U.S.A.) after purification of the reaction product using an integrated HPLC instrument (Agilent 1100 Series HPLC System). As can be seen, the theoretical and experimental mass spectra are in excellent agreement, thus clearly suggesting the formation of the Vancomycin:Gibbs reaction product.

Figure 5:
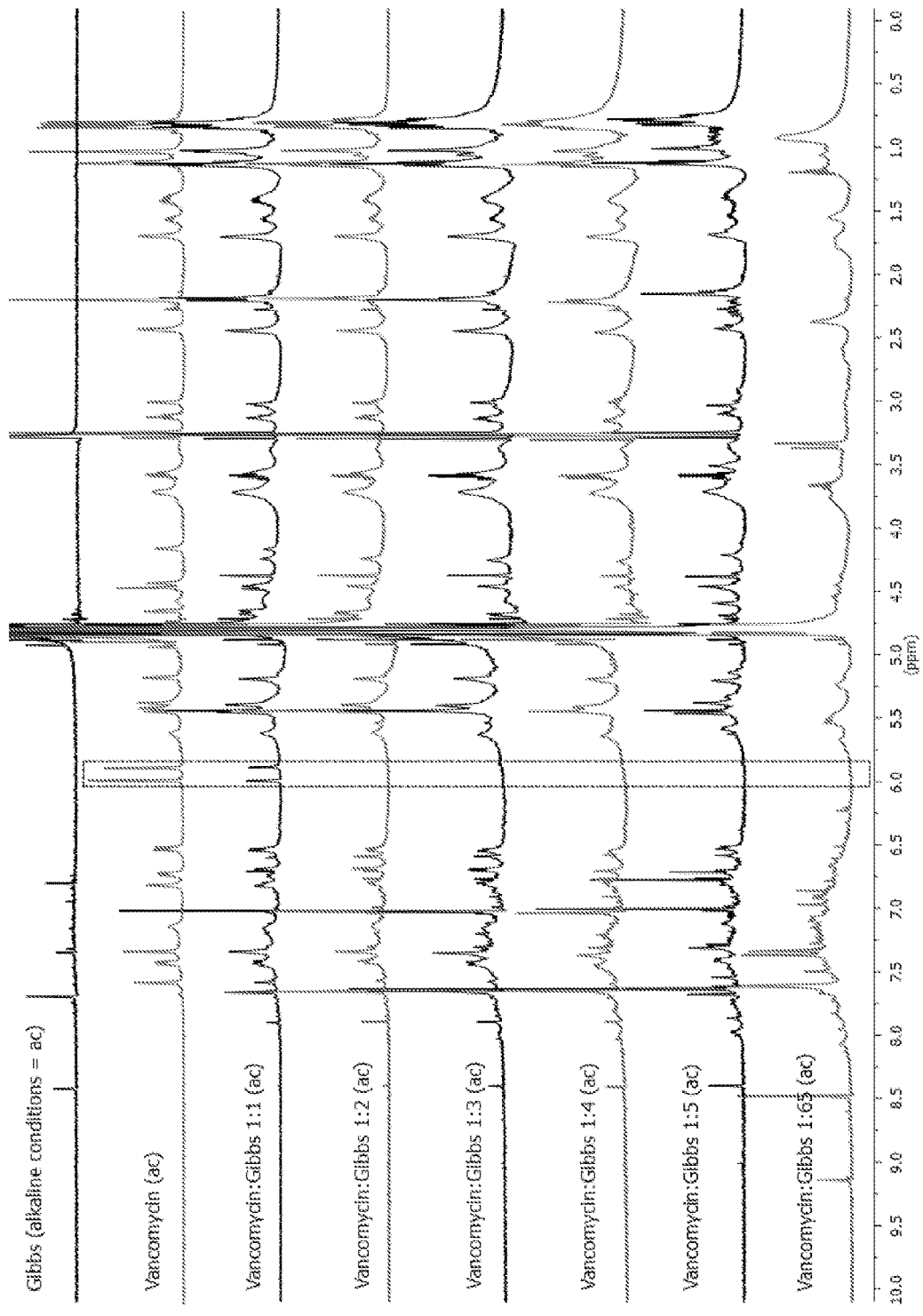
FIG. 5 depicts $^1$H-NMR spectra of the Vancomycin-Gibbs reagent reaction product for a number of Vancomycin:Gibbs molar reagent ratios.

FIG. 5 shows the several $^1$H-NMR spectra including starting materials Vancomycin and Gibbs reagent both under alkaline conditions and several reactions with the increasing equivalents of Gibbs reagent used in the synthesis example 1. The NMR spectra were recorded on an Avance III 600 Cryo NMR spectrometer from Bruker (Bruker, Billerica, Mass., U.S.A.) in ⅓ $D_2O$+⅔ MeOD by volume with 0.4 M NaOD in $D_2O$. The water peak was used for PPM calibration. The disappearance of the two peaks just below 6 ppm highlighted with a dotted box with increasing Gibbs equivalent provides clear evidence that Gibbs is coupling to the aromatic ring indicated in Reaction Scheme 1. The assignment of all other Vancomycin protons which remained unchanged due to the Gibbs addition is in good agreement with Antipas et al., Journal of Pharmaceutical Sciences 88(6), pages 742-750, 2000 and Pearce and Williams, J.

Chem. Soc., Perkin Trans. 2(1), pages 153-157, 1995, which disclose the 1H NMR spectrum of Vancomycin.

Example 1

A 1 ml whole serum sample spiked with Vancomycin is applied to a 30 mg/1 ml reversed phase Strata-X™ SPE column from Phenomenex®. The column is washed firstly with 2 ml water to remove weakly bound impurities; followed by a wash with approximately 2 ml of pure organic solvents such as, but not limited to, methanol, to remove lipophilic respectively hydrophobic species, which may interfere with the coupling reaction and may lead to cross-contamination, such as, but not limited to, propofol. The Vancomycin bound to serum constituents present in the whole serum sample is then eluted from the SPE column using a known volume (0.5 ml) of a mixture of one-third water and two-thirds methanol (both by volume).

A 350 µl fraction of the elute is then transferred into a vial. Then 50 µl of 3.625 mM Gibbs in methanol is added, followed by 40 µl of 0.4 M sodium hydroxide in borate buffer or water, which initiates the coupling reaction and results in an immediate colour change. After a shake, typically 350 µl of the mixture is transferred into a cuvette and its spectra is measured via a spectrophotometer.

Comparative Example 1

Comparative example 1 is the same as example 1 with the difference that a 1 ml whole serum sample without Vancomycin is applied to a 30 mg/1 ml reversed phase Strata-X™ SPE column.

Figure 6:
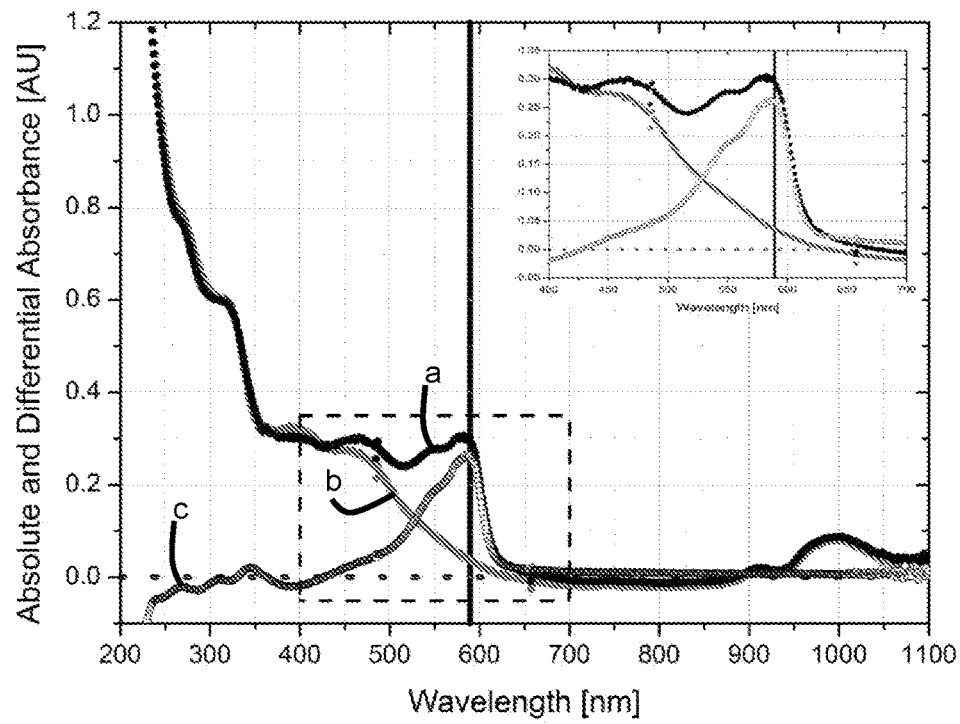
FIG. 6-7 depict absorption characteristics of the reaction of Vancomycin extracted from a complex sample matrix with the activated Gibbs reagent.

FIG. 6 shows the typical UV/vis spectra of Gibbs labelling of two SPE elutes from serum, sample (a) spiked with Vancomycin from example 1, and a reference (b) without Vancomycin from comparative example 1. The spectrum (c) is the difference between the sample and reference spectrum. The absorbance at 589 nm suggests that Vancomycin can be recovered out of the complex sample matrix via Strata-X and subsequently labelled with Gibbs reagent in a comparable manner and in very good agreement with synthesis example 1 and FIG. 3. The corresponding Vancomycin concentration can then be calculated via the Beer-Lambert law.

Example 2

Figure 7:
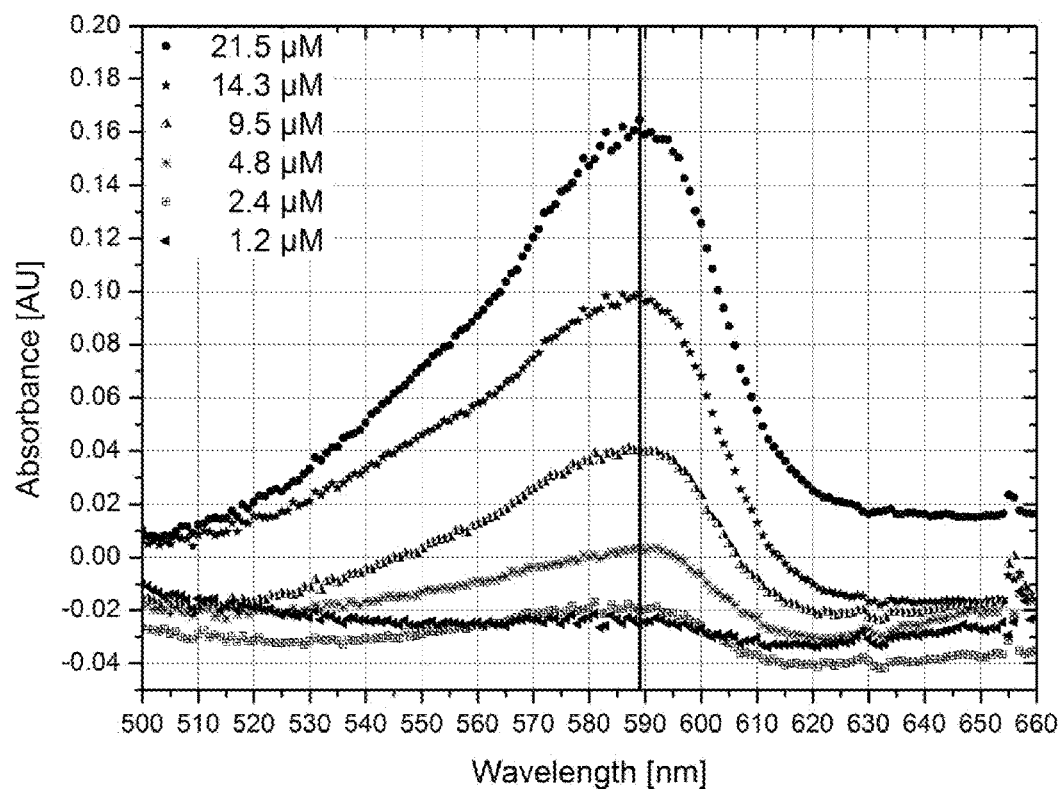

In order to verify the accuracy of the present method, whole blood serums were spiked with different Vancomycin concentrations (1.2 µM, 2.4 µM, 4.8 µM, 9.5 µM, 14.3 µM and 21.5 µM respectively) and passed over the assay as described in example 1. Two fractions of each elute were independently labelled with the Gibbs reagent to get an estimation of the accuracy of the novel Vancomycin assay. FIG. 7 shows the UV-vis differential absorption spectra of the various eluents after completing the Gibbs reaction against the reference of comparative example 1, which clearly demonstrates that with this novel assay detection of Vancomycin in the therapeutic window, 3-29 µM, is achievable.

Figure 8:
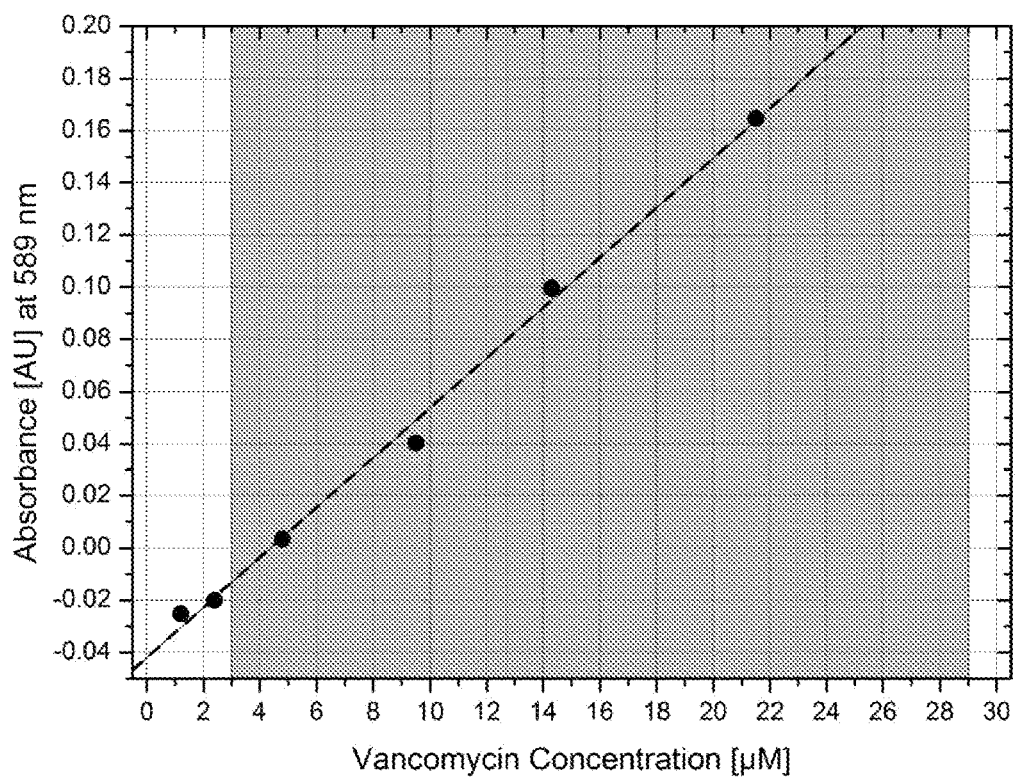
FIG. 8 depicts a fit of measured differential absorbance as determined using an embodiment of the colourimetric method of the present invention against known vancomycin concentrations in eluent solutions.

This is further corroborated by FIG. 8, which depicts a linear fit of the eluent concentrations as obtained from the differential absorption spectra at 589 nm using a fitting function y=a+b*x, in which a was found to be −0.042±0.004; b was found to be 0.01±0.004 with a $R^2$ value of 0.994, thus demonstrating an excellent fit between the spike levels and the concentrations obtained from the eluent extracted from the serum samples including these spike levels.

Example 3

A 1 ml whole serum sample (VVHS) spiked with Vancomycin is applied to a 30 mg/1 ml reversed phase Strata-X™ SPE column from Phenomenex®. The column is washed firstly with 2 ml water to remove weakly bound impurities. This washing step may be repeated if necessary. Then a known volume (1 ml) of an organic solvent such as, but not limited to, methanol is used to elute the free Vancomycin fraction from the sorbent. This optionally may be followed by another organic washing step, e.g. another washing step with an organic solvent, which may be the same solvent or a different solvent as used in the elution step. The bound Vancomycin fraction is then eluted from the SPE column using a known volume (0.5 ml) of a mixture of one-third water and two-thirds methanol (by volume).

A 350 µl fraction of each elute is then transferred into separate vials. Then 50 µl of 3.625 mM Gibbs in methanol is added to each vial, followed by 40 µl of 0.4 M sodium hydroxide in borate buffer or water, which initiates the coupling reaction and results in an immediate colour change. After a shake, typically 350 µl of each mixture is transferred into a cuvette and their spectra are measured via a spectrophotometer.

Figure 9:
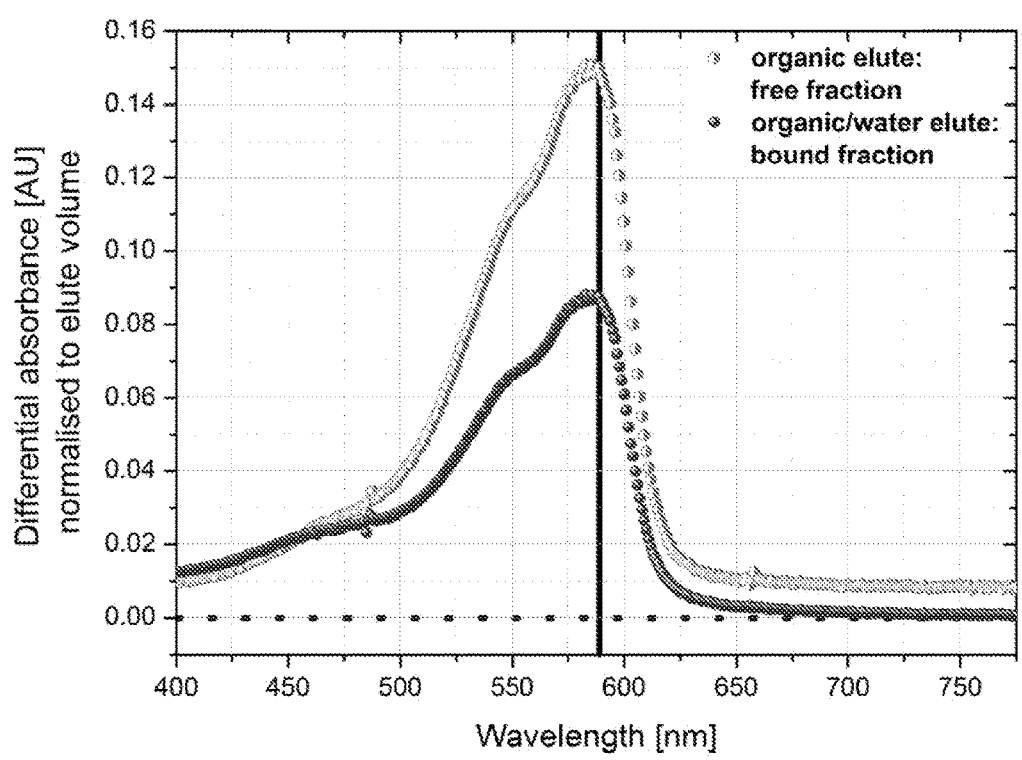
FIG. 9 depicts absorption characteristics of the reaction of Vancomycin extracted from a complex sample matrix with the activated Gibbs reagent in accordance with another embodiment of the present invention.

FIG. 9 shows the differential UV-vis spectra of the free and bound fractions of the same WHS sample spiked with 29 µM Vancomycin, which were subtracted from comparative example 3. The maximal absorbance wavelength ($\lambda_{max}$) of the newly formed coupling product is 589 nm (highlighted by a vertical line in the graph) and the corresponding free and bound concentrations can be calculated via the Beer-Lambert law.

Comparative Example 2

Comparative Example 2 is the same as example 3 with the difference that a 1 ml whole serum sample without Vancomycin is applied to a 30 mg/1 ml reversed phase Strata-X™ SPE column.

Example 4

In order to verify the accuracy of the method presented in Example 3, samples with several different serum protein concentrations, herein human serum albumin (HSA) (600 µM, 300 µM, 150 µM, 75 µM and 0 µM) dissolved in water, as well as whole human serum (WHS) were spiked with the same Vancomycin concentration (29 µM). It is noted that 600 µM corresponds to the concentration of serum albumin in whole human serum. These samples were passed over the assay as described in Example 3. Collection from both elutes, the organic elute and the mixture of one-third water and two-thirds methanol (by volume) elute, were independently labelled with the Gibbs reagent to get an estimation of the accuracy of the novel free and bound Vancomycin assay.

Figure 10:
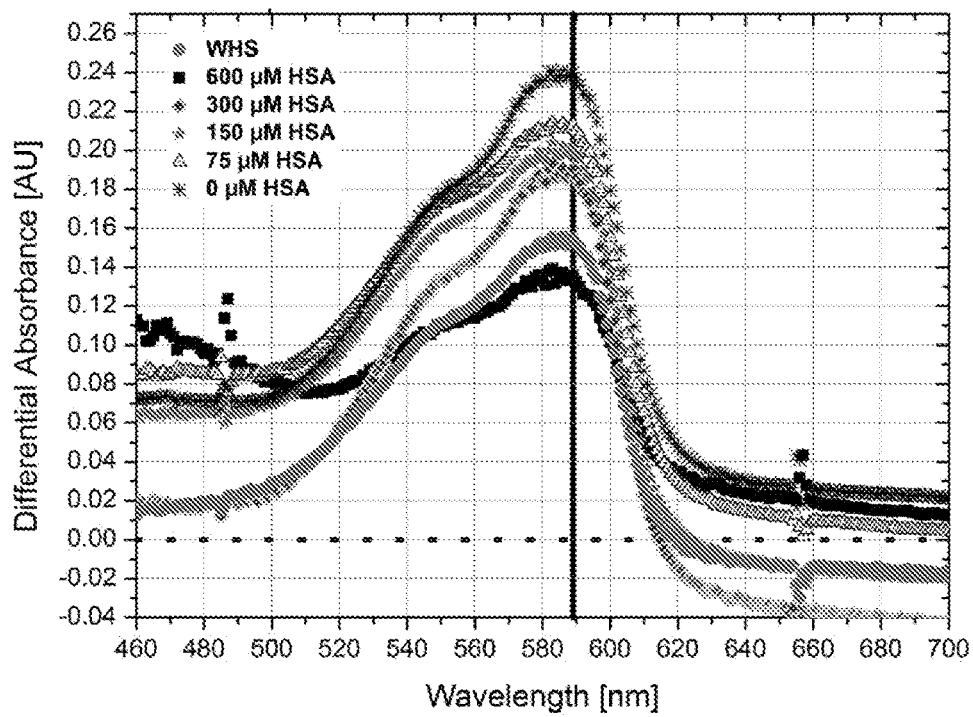
FIG. 10 depicts absorption characteristics of the reaction of free Vancomycin (A) and protein-bound Vancomycin (B) extracted from a number of complex sample matrices comprising different protein concentrations with the activated Gibbs reagent in accordance with another embodiment of the present invention.
Figure 10:
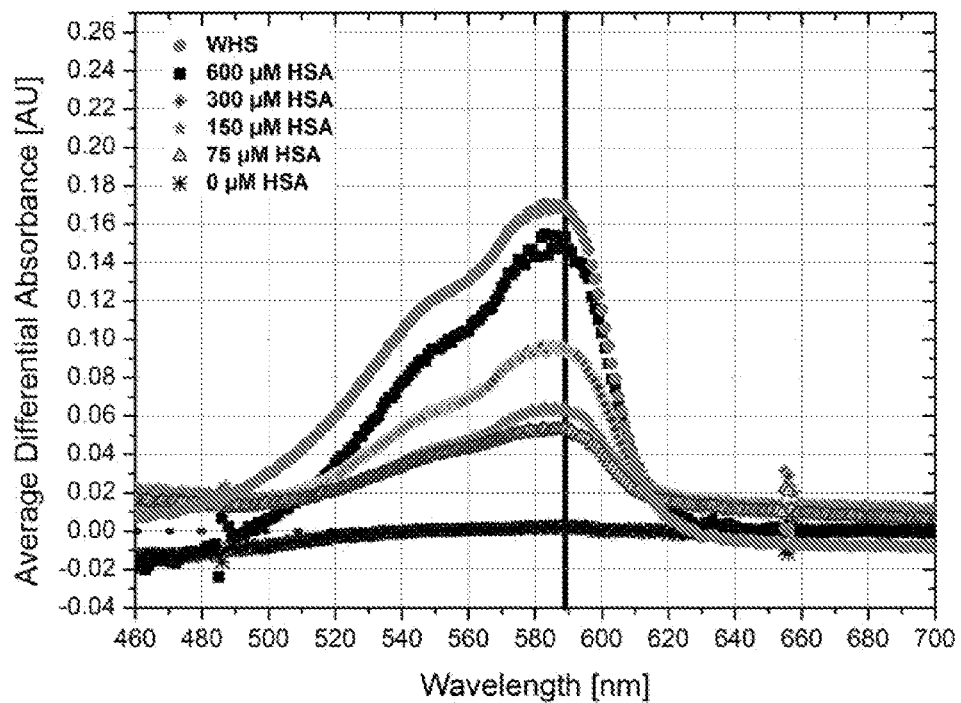
Figure 11:
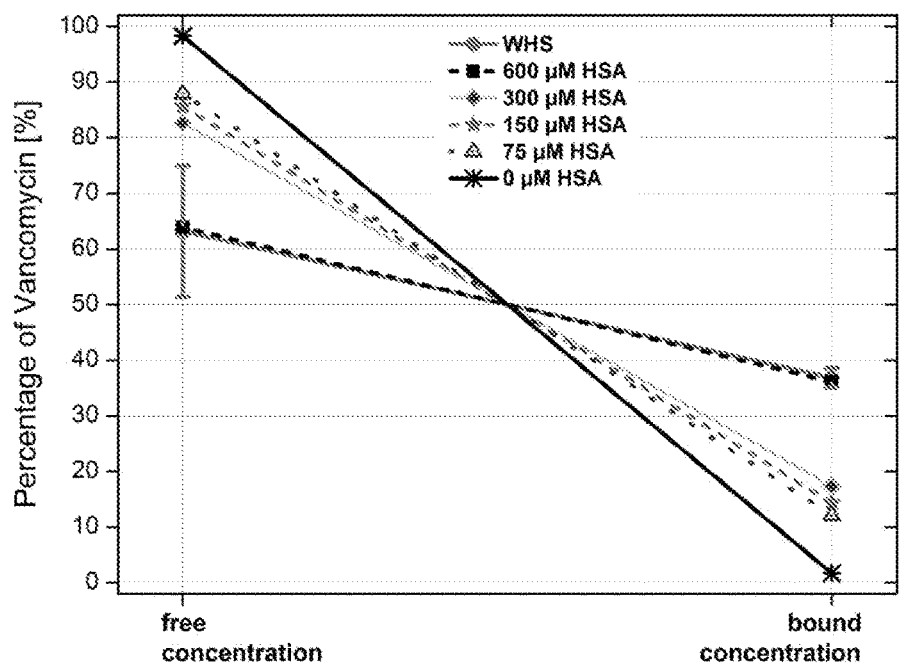
FIG. 11 is a plot of the ratios of free and protein-bound Vancomycin concentrations as extracted from the complex sample matrices shown in FIG. 10.

FIGS. 10A and B show the differential absorbencies of the organic (A) and the mixed water/organic (B) elutes respectively for the several protein concentrations and whole human serum (WHS) captured via UV-vis spectroscopy. The corresponding absorbencies values for free and bound at the maximal absorbance wavelength ($\lambda_{max}$=589 nm) of the novel coupling product were used to calculate the percentages of Vancomycin [%] comprised in the free and bound fractions, which is graphically illustrated in FIG. 11.

For commercially available whole human serum typically 63±12% was found to be free and 37±2% to be bound. The errors are derived from the standard deviation from three independent measurements (n=3) indicated by the error bars in the FIG. 11.

Example 5

In order to demonstrate the specificity of the extraction protocol for glycopeptide antibiotics with one or more phenolic moieties such as Vancomycin, four whole serum samples were prepared with 0.1 μM Dopamine, 132 μM Paracetamol and 56.1 μM Propofol as potentially interfering phenolic compounds and 29 μM Vancomycin. The column is firstly twice washed with 2 ml water to remove weakly bound impurities. Then a known volume (1 ml) of methanol is used to elute the free Vancomycin fraction from the sorbent. This optionally may be followed by another organic washing step, e.g. another washing step with methanol. The bound Vancomycin fraction is then eluted from the SPE column using a known volume (0.5 ml) of a mixture of one-third water and two-thirds methanol (by volume).

Figure 12:
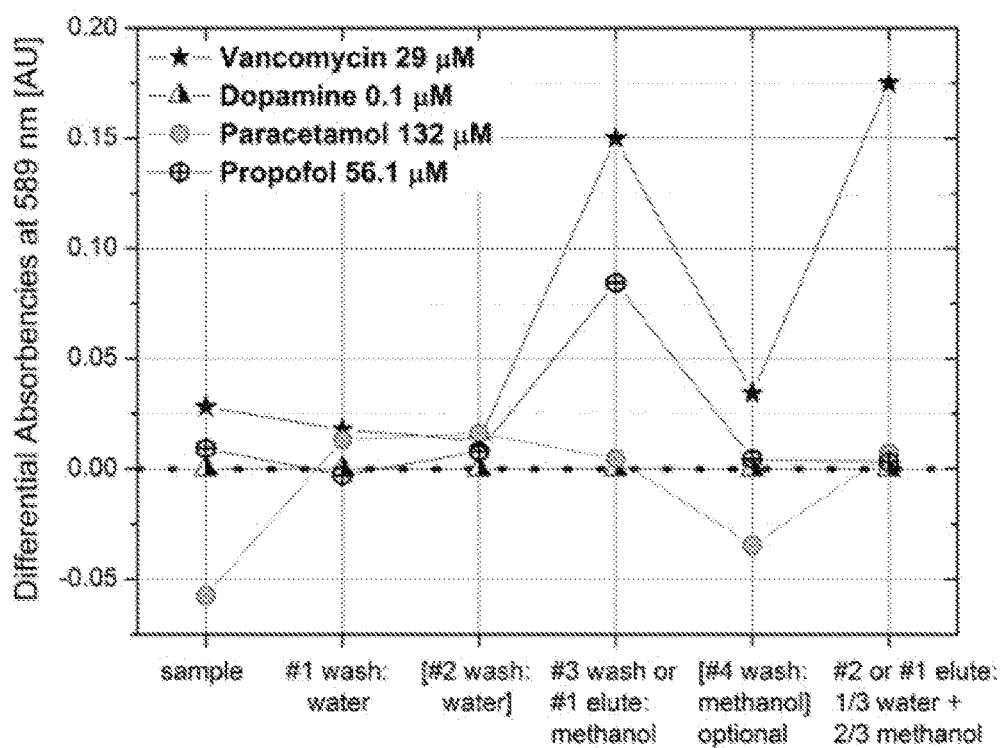
FIG. 12 depicts an absorption characteristics comparison of the Gibbs reaction product of Vancomycin and other phenolic compounds extracted from whole serum samples.

After each washing/elution step, the washing agent/eluent was collected and reacted with the Gibbs reagent using the reaction conditions of Example 1 and the reaction product was evaluated as explained in Example 1. The results are shown in FIG. 12.

It can be seen that the first and second washing steps with water remove negligible amounts of the phenolic compounds from the sorbent material, but that the first methanol eluent removes the unbound fraction of Vancomycin as previously demonstrated as well as at least some of the Propofol. The optional subsequent washing step with methanol further removes some of the Vancomycin, such that the first eluent may be combined with the methanol used in this washing step to further improve the accuracy of the unbound Vancomycin determination. The second eluent (methanol/water) removes the bound fraction of Vancomycin at excellent specificity.

It therefore has been demonstrated that glycopeptide antibiotics such as Vancomycin can be removed with good selectivity from the sorbent material using the proposed extraction protocol in the presence of other phenolic compounds. It is noted that Propofol shows some interference in the first eluent (methanol) but this does not affect the determination of the bound fraction of the glycopeptide antibiotic, which is derived from the second eluent.

In order to avoid potential interference of Propofol in the determination of the unbound fraction of the glycopeptide antibiotic, the following measures may be considered. Since Propofol does not naturally occur in patients, the unbound fraction of a glycopeptide antibiotic such as Vancomycin may be determined when the patient is not under the influence of Propofol. Alternatively, the Propofol concentration may be determined independently on a separate extraction assay, e.g. using the protocols disclosed in WO 2012/049486 A1 such that the contribution of Propofol to the overall determination can be subtracted to yield the unbound glycopeptide antibiotic concentration.

Figure 13:
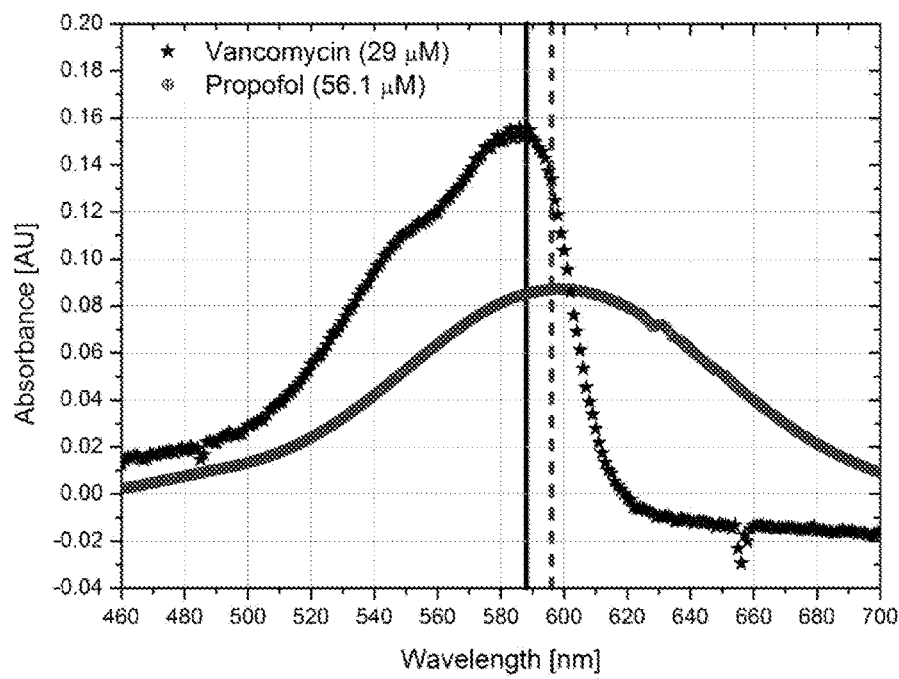
FIG. 13 depicts an absorbance spectrum of the Gibbs reaction product of Vancomycin and Propofol.

Moreover, since the Propofol/Gibbs reaction product is blue and consequently has a $\lambda_{max}$ of 595 nm and Vancomycin/Gibbs reaction product is purple/magenta with $\lambda_{max}$ of 589 nm, see FIG. 13, measuring the UV/vis spectrum over an appropriate spectral range instead of at a fixed wavelength (i.e. at 589 nm) may allow for the extraction of the propofol contribution from the overall determined concentration. For instance, by measuring the absorbance in a window from for instance from 500-700 nm, the shoulder appearing above 600 nm that is caused by the concentration of Propofol:Gibbs reaction product present in the sample can be used to calculate, e.g. subtract, the contribution of the Propofol:Gibbs reaction product to the absorbance at 589 nm.

Figure 14:
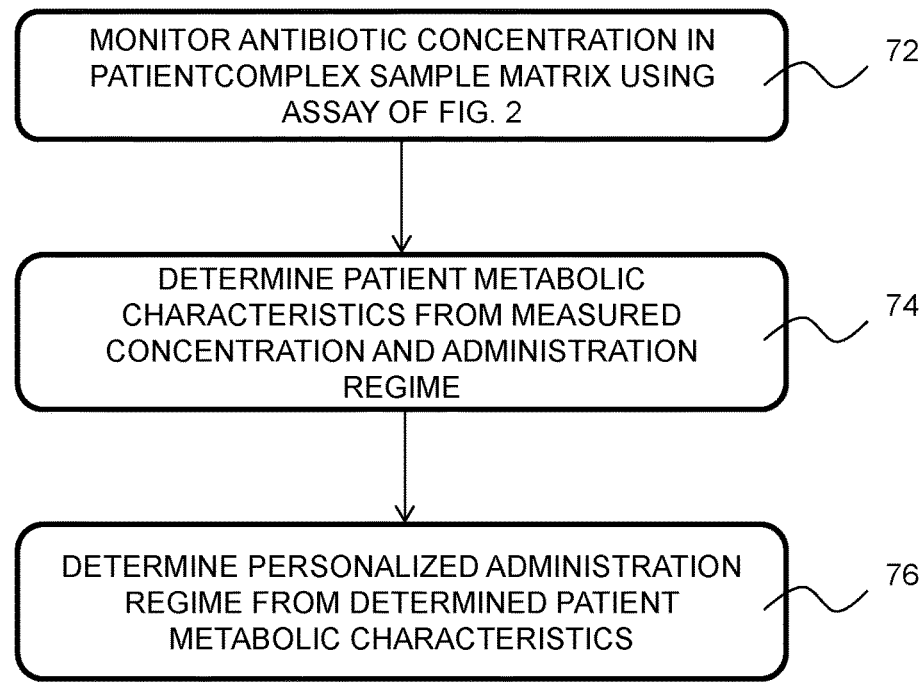
FIG. 14 is a flow chart of another method of the present invention.

As can be seen from FIG. 6-13, it is possible to accurately determine the Vancomycin levels within its therapeutic window, which for instance has been identified in FIG. 8 by the shaded area. This can be advantageously used to personalized administration regime of an antibiotic containing a phenol moiety such as Vancomycin for a patient. An example of such a method of determining a personalized administration regime of an antibiotic containing a phenol moiety such as Vancomycin for a patient using the present invention is shown in FIG. 14.

In step 72, the concentration of the antibiotic in a complex sample matrix of said patient is determined in accordance with an embodiment of the method of the present invention as described in detail above with the aid of FIG. 1. In step 74, the determined concentration is compared against the administered amount of the phenol moiety-containing antibiotic, e.g. Vancomycin, to derive the metabolic characteristics of the antibiotic in the patient. In particular, it may be determined if the determined concentration still falls within the therapeutic window of the antibiotic.

In an embodiment, step 72 may comprise periodically determining the concentration of the antibiotic in a complex sample matrix of said patient before deriving the metabolic characteristics of the antibiotic in the patient, as such periodic measurements can be used to determine a trend in the determined concentrations, thus giving further insight the metabolic characteristics of the antibiotic in the patient. For instance, such a trend may indicate the metabolic rate for an administered amount of the antibiotic.

In step 76, the determined metabolic characteristics of the antibiotic in the patient are used to design a personalized antibiotic administration regime for the patient to ensure that the amount of the antibiotic in the patient's metabolism remains within the therapeutic window, thus significantly reducing the risk that the treatment is ineffective, with the potential grave consequence of the microbial target of the treatment becoming resistant to the administered antibiotic, e.g. Vancomycin.

At this point it is noted that the Gibbs reaction involving the phenol functional group containing antibiotic, e.g. Vancomycin preferably is performed following the extraction of the antibiotic from the sorbent and/or filter material, i.e. in the eluent.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

What is claimed is:

1. A method of determining a concentration of a glycopeptide antibiotic containing a phenol moiety in a complex sample matrix, the method comprising:
   extracting the glycopeptide antibiotic from a metered portion of the complex sample matrix by:
   exposing said metered portion of the complex sample matrix to an extraction material having an affinity with the glycopeptide antibiotic; and
   exposing the extraction material to a metered portion of a first eluent being a first organic solvent or a second eluent being a second organic solvent/water mixture for releasing the glycopeptide antibiotic from the extraction material; and
   determining a concentration of the glycopeptide antibiotic by:
   adding an excess amount of Gibbs reagent (2,6 dichloroquinone-4-chloroimide) relative to the amount of the glycopeptide antibiotic containing a phenol moiety to the metered portion of the first or second eluent;
   activating the Gibbs reagent under alkaline conditions and, after the reaction between the activated Gibbs reagent and the glycopeptide antibiotic has stabilized;
   detecting the reaction product of the activated Gibbs reagent and the glycopeptide antibiotic in said metered portion of the first or second eluent; and
   determining a concentration of the glycopeptide antibiotic in the complex sample matrix from the detected reaction product, said concentration being:
   the concentration of unbound glycopeptide antibiotic in the complex sample matrix in case of the first eluent; or
   the concentration of bound glycopeptide antibiotic in the complex sample matrix in case of the second eluent, and
   wherein the step of exposing the extraction material to a metered portion of a first or second eluent is performed with the first eluent and the concentration of the glycopeptide antibiotic in the complex sample matrix from the detected reaction product is the concentration of unbound glycopeptide antibiotic in the complex sample matrix, the method further comprising the step of exposing the extraction material to a metered portion of the second eluent and the concentration of the glycopeptide antibiotic in the complex sample matrix from the detected reaction product is the concentration of bound glycopeptide antibiotic in the complex sample matrix.

2. The method of claim 1, wherein the first and/or the second organic solvent is methanol.

3. A method of determining a concentration of a glycopeptide antibiotic containing a phenol moiety in a complex sample matrix, the method comprising:
   extracting the glycopeptide antibiotic from a metered portion of the complex sample matrix by:
   exposing said metered portion of the complex sample matrix to an extraction material having an affinity with the glycopeptide antibiotic; and
   exposing the extraction material to a metered portion of a first eluent being a first organic solvent or a second eluent being a second organic solvent/water mixture for releasing the glycopeptide antibiotic from the extraction material; and
   determining a concentration of the glycopeptide antibiotic by:
   adding an excess amount of Gibbs reagent (2,6 dichloroquinone-4-chloroimide) relative to the amount of the glycopeptide antibiotic containing a phenol moiety to the metered portion of the first or second eluent;
   activating the Gibbs reagent under alkaline conditions and, after the reaction between the activated Gibbs reagent and the glycopeptide antibiotic has stabilized;
   detecting the reaction product of the activated Gibbs reagent and the glycopeptide antibiotic in said metered portion of the first or second eluent; and
   determining a concentration of the glycopeptide antibiotic in the complex sample matrix from the detected reaction product, said concentration being:
   the concentration of unbound glycopeptide antibiotic in the complex sample matrix in case of the first eluent; or
   the concentration of bound glycopeptide antibiotic in the complex sample matrix in case of the second eluent, and
   wherein the second eluent is a methanol/water mixture in a 2:1 ratio by volume.

4. A method of determining a concentration of a glycopeptide antibiotic containing a phenol moiety in a complex sample matrix, the method comprising:
   extracting the glycopeptide antibiotic from a metered portion of the complex sample matrix by:
   exposing said metered portion of the complex sample matrix to an extraction material having an affinity with the glycopeptide antibiotic; and
   exposing the extraction material to a metered portion of a first eluent being a first organic solvent or a second eluent being a second organic solvent/water mixture for releasing the glycopeptide antibiotic from the extraction material; and
   determining a concentration of the glycopeptide antibiotic by:
   adding an excess amount of Gibbs reagent (2,6 dichloroquinone-4-chloroimide) relative to the amount of the glycopeptide antibiotic containing a phenol moiety to the metered portion of the first or second eluent;
   activating the Gibbs reagent under alkaline conditions and, after the reaction between the activated Gibbs reagent and the glycopeptide antibiotic has stabilized;
   detecting the reaction product of the activated Gibbs reagent and the glycopeptide antibiotic in said metered portion of the first or second eluent; and
   determining a concentration of the glycopeptide antibiotic in the complex sample matrix from the detected reaction product, said concentration being:
   the concentration of unbound glycopeptide antibiotic in the complex sample matrix in case of the first eluent; or
   the concentration of bound glycopeptide antibiotic in the complex sample matrix in case of the second eluent, and
   further comprising exposing the extraction material to at least one washing step prior to exposing the extraction material to said metered portion of the first or second eluent to remove weakly bound impurities from the extraction material.

5. The method of claim 1, wherein the complex sample matrix comprises cellular material, and wherein the step of exposing said metered portion of the complex sample matrix to an extraction material having an affinity with the glycopeptide antibiotic comprises:
   providing a known quantity of the complex sample matrix;
   diluting said known quantity with a lysing agent, said lysing agent having an osmotic pressure lower than the osmotic pressure of the cellular material, to provide destabilized cellular material; and subsequently feeding the diluted known quantity through a filtering stage comprising the extraction material after a predetermined amount of time to separate the glycopeptide antibiotic from the destabilized cellular material by selectively adhering the glycopeptide antibiotic to the extraction material.

6. The method of claim 5, wherein the extraction material comprises a sorbent material for mechanically lysing the cellular material, said sorbent material having an affinity for binding the glycopeptide antibiotic.

7. The method of claim 6, wherein said sorbent material is a reverse phase sorbent material.

8. The method of claim 1, wherein said detecting step comprises electrochemically or colorimetrically detecting the reaction product of the activated Gibbs reagent and the glycopeptide antibiotic.

9. The method of claim 8, wherein said colorimetrically detecting comprises measuring the intensity of an absorption in a range of 580-600 nm.

10. The method of claim 1, wherein the glycopeptide antibiotic is Vancomycin.

11. The method of claim 1, wherein the complex sample matrix is one of blood, plasma and serum or is obtained from a food product.

12. A method of providing a personalized administration regime of a glycopeptides antibiotic containing a phenol moiety for a patient, the method comprising:

determining the concentration of the glycopeptide antibiotic in a complex sample matrix of said patient in accordance with the method of any one of claims 1, 3 or 4;

deriving metabolic characteristics of the glycopeptide antibiotic for said patient from the determined concentration of the glycopeptide antibiotic in said complex sample matrix; and providing said personalized glycopeptide antibiotic administration regime based on said metabolic characteristics.

13. The method of claim 12, wherein said determining step comprises periodically determining the concentration of the glycopeptide antibiotic, and wherein said deriving step comprises deriving said metabolic characteristics from a trend in the periodically determined concentrations.

14. The method of claim 7, wherein the reverse phase sorbent material is C8, C12, C18 or Strata-X.

15. The method of claim 9, wherein the colorimetrically detecting comprises measuring the intensity of an absorption at 589 nm.

16. The method of claim 11, wherein the food product is milk or meat.

* * * * *